US012098394B2

(12) United States Patent
Hong et al.

(10) Patent No.: US 12,098,394 B2
(45) Date of Patent: Sep. 24, 2024

(54) MONOOXYGENASE MUTANT AND USE THEREOF

(71) Applicant: ASYMCHEM LABORATORIES (TIANJIN) CO., LTD., Tianjin (CN)

(72) Inventors: Hao Hong, Morrisville, NC (US); Gage James, Morrisville, NC (US); Jiangping Lu, Tianjin (CN); Xuecheng Jiao, Tianjin (CN); Na Zhang, Tianjin (CN); Kejian Zhang, Tianjin (CN); Rui Li, Tianjin (CN); Yu Zhang, Tianjin (CN); Yiming Yang, Tianjin (CN)

(73) Assignee: ASYMCHEM LABORATORIES (TIANJIN) CO., LTD., Tianjin (CN)

( * ) Notice: Subject to any disclaimer, the term of this patent is extended or adjusted under 35 U.S.C. 154(b) by 84 days.

(21) Appl. No.: 17/290,749

(22) PCT Filed: Nov. 5, 2018

(86) PCT No.: PCT/CN2018/113938

§ 371 (c)(1), (2) Date: Apr. 30, 2021

(87) PCT Pub. No.: WO2020/093191

PCT Pub. Date: May 14, 2020

(65) Prior Publication Data

US 2022/0002683 A1 Jan. 6, 2022

(51) Int. Cl.
*C12N 9/04* (2006.01)
*C12P 11/00* (2006.01)

(52) U.S. Cl.
CPC ............ *C12N 9/0006* (2013.01); *C12P 11/00* (2013.01)

(58) Field of Classification Search
CPC ...... C12N 9/0006; C12N 9/0073; C12P 11/00
See application file for complete search history.

(56) References Cited

FOREIGN PATENT DOCUMENTS

| | | | |
|---|---|---|---|
| CN | 105695425 | A | 6/2016 |
| CN | 106754802 | A | 5/2017 |
| CN | 108300707 | A | 7/2018 |
| WO | 0142436 | A2 | 6/2001 |
| WO | 0142436 | A3 | 11/2001 |

OTHER PUBLICATIONS

GenBank accession No. WP_110694042, Jul. 8, 2018.*
Gomez-Escribano, GenBank accession No. CQR60781, May 21, 2015.*
Witkowski et al., Biochemistry 38:11643-11650, 1999.*
Tang et al., Phil Trans R Soc B 368:20120318, 1-10, 2013.*
Seffernick et al., J. Bacteriol. 183(8):2405-2410, 2001.*
Singh et al., Current Protein and Peptide Science 19(1):5-15, 2018.*
Sadowski et al., Current Opinion in Structural Biology 19:357-362, 2009.*
GenBank Accession No. AAL14233; GenBank Database, Oct. 17, 2001.
Liang, Qiuling et al.; Nonconserved Hinge in Baeyer-Villiger Monooxygenase Affects Catalytic Activity and Stereoselectivity; Chinese Journal of Biotechnology, vol. 31, No. 3, Mar. 25, 2015, ISSN: 1000-361, pp. 361-374.
Kostichka, Kristy et al; "Cloning and Characterization of a Gene Cluster for Cyclododecanone Oxidation in Rhodococcus ruber SC1"; Journal of Bacteriology; vol. 183, No. 21; Nov. 2001; pp. 6478-6486.
Database Uniprot; "monooxygenase from *Atreptosporangium* sp.'*caverna*' "; Database Accession No. AoA2Z3UFR4; Oct. 10, 2018; sequence.
"R. ruber cyclododecanone monooxygenase enzyme"; Database acession No. AAB85324; Jun. 15, 2007; sequence.

* cited by examiner

*Primary Examiner* — Delia M Ramirez
(74) *Attorney, Agent, or Firm* — NKL LAW; Allen Xue

(57) ABSTRACT

An amino acid sequence of the monooxygenase mutant is obtained by mutation of an amino acid sequence shown in SEQ ID NO: 1, and the mutation at least includes one of the following mutation sites: 45-th site, 95-th site, 106-th site, 108-th site, 114-th site, 186-th site, 190-th site, 191-th site, 249-th site, 257-th site, 393-th site, 436-th site, 499-th site, 500-th site, 501-th site, 503-th site, 504-th site, 559-th site, and 560-th site.

9 Claims, No Drawings

Specification includes a Sequence Listing.

SEQUENCE LISTING

```
<160> NUMBER OF SEQ ID NOS: 2

<210> SEQ ID NO 1
<211> LENGTH: 603
<212> TYPE: PRT
<213> ORGANISM: Rhodococcus ruber

<400> SEQUENCE: 1

Met Thr Thr Ser Ile Asp Arg Glu Ala Leu Arg Arg Lys Tyr Ala Glu
1               5                   10                  15

Glu Arg Asp Lys Arg Ile Arg Pro Asp Gly Asn Asp Gln Tyr Ile Arg
            20                  25                  30

Leu Asp His Val Asp Gly Trp Ser His Asp Pro Tyr Met Pro Ile Thr
        35                  40                  45

Pro Arg Glu Pro Lys Leu Asp His Val Thr Phe Ala Phe Ile Gly Gly
    50                  55                  60

Gly Phe Ser Gly Leu Val Thr Ala Ala Arg Leu Arg Glu Ser Gly Val
65                  70                  75                  80

Glu Ser Val Arg Ile Ile Asp Lys Ala Gly Asp Phe Gly Gly Val Trp
                85                  90                  95

Tyr Trp Asn Arg Tyr Pro Gly Ala Met Cys Asp Thr Ala Ala Met Val
            100                 105                 110

Tyr Met Pro Leu Leu Glu Glu Thr Gly Tyr Met Pro Thr Glu Lys Tyr
        115                 120                 125

Ala His Gly Pro Glu Ile Leu Glu His Cys Gln Arg Ile Gly Lys His
    130                 135                 140

Tyr Asp Leu Tyr Asp Asp Ala Leu Phe His Thr Glu Val Thr Asp Leu
145                 150                 155                 160

Val Trp Gln Glu His Asp Gln Arg Trp Arg Ile Ser Thr Asn Arg Gly
                165                 170                 175

Asp His Phe Thr Ala Gln Phe Val Gly Met Gly Thr Gly Pro Leu His
            180                 185                 190

Val Ala Gln Leu Pro Gly Ile Pro Gly Ile Glu Ser Phe Arg Gly Lys
```

```
        195                 200                 205

Ser Phe His Thr Ser Arg Trp Asp Tyr Asp Tyr Thr Gly Gly Asp Ala
    210                 215                 220

Leu Gly Ala Pro Met Asp Lys Leu Ala Asp Lys Arg Val Ala Val Ile
225                 230                 235                 240

Gly Thr Gly Ala Thr Ala Val Gln Cys Val Pro Glu Leu Ala Lys Tyr
                245                 250                 255

Cys Arg Glu Leu Tyr Val Val Gln Arg Thr Pro Ser Ala Val Asp Glu
            260                 265                 270

Arg Gly Asn His Pro Ile Asp Glu Lys Trp Phe Ala Gln Ile Ala Thr
        275                 280                 285

Pro Gly Trp Gln Lys Arg Trp Leu Asp Ser Phe Thr Ala Ile Trp Asp
    290                 295                 300

Gly Val Leu Thr Asp Pro Ser Glu Leu Ala Ile Glu His Glu Asp Leu
305                 310                 315                 320

Val Gln Asp Gly Trp Thr Ala Leu Gly Gln Arg Met Arg Ala Ala Val
                325                 330                 335

Gly Ser Val Pro Ile Glu Gln Tyr Ser Pro Glu Asn Val Gln Arg Ala
            340                 345                 350

Leu Glu Glu Ala Asp Asp Glu Gln Met Glu Arg Ile Arg Ala Arg Val
        355                 360                 365

Asp Glu Ile Val Thr Asp Pro Ala Thr Ala Ala Gln Leu Lys Ala Trp
    370                 375                 380

Phe Arg Gln Met Cys Lys Arg Pro Cys Phe His Asp Asp Tyr Leu Pro
385                 390                 395                 400

Ala Phe Asn Arg Pro Asn Thr His Leu Val Asp Thr Gly Gly Lys Gly
                405                 410                 415

Val Glu Arg Ile Thr Glu Asn Gly Val Val Val Ala Gly Val Glu Tyr
            420                 425                 430

Glu Val Asp Cys Ile Val Tyr Ala Ser Gly Phe Glu Phe Leu Gly Thr
        435                 440                 445

Gly Tyr Thr Asp Arg Ala Gly Phe Asp Pro Thr Gly Arg Asp Gly Val
    450                 455                 460

Lys Leu Ser Glu His Trp Ala Gln Gly Thr Arg Thr Leu His Gly Met
465                 470                 475                 480

His Thr Tyr Gly Phe Pro Asn Leu Phe Val Leu Gln Leu Met Gln Gly
                485                 490                 495

Ala Ala Leu Gly Ser Asn Ile Pro His Asn Phe Val Glu Ala Ala Arg
            500                 505                 510

Val Val Ala Ala Ile Val Asp His Val Leu Ser Thr Gly Thr Ser Ser
        515                 520                 525

Val Glu Thr Thr Lys Glu Ala Glu Gln Ala Trp Val Gln Leu Leu Leu
    530                 535                 540

Asp His Gly Arg Pro Leu Gly Asn Pro Glu Cys Thr Pro Gly Tyr Tyr
545                 550                 555                 560

Asn Asn Glu Gly Lys Pro Ala Glu Leu Lys Asp Arg Leu Asn Val Gly
                565                 570                 575

Tyr Pro Ala Gly Ser Ala Ala Phe Phe Arg Met Met Asp His Trp Leu
            580                 585                 590

Ala Ala Gly Ser Phe Asp Gly Leu Thr Phe Arg
        595                 600
```

<210> SEQ ID NO 2

-continued

```
<211> LENGTH: 1812
<212> TYPE: DNA
<213> ORGANISM: Rhodococcus ruber

<400> SEQUENCE: 2

atgacaacca gtatcgatcg cgaggccctg cgccgcaaat atgccgaaga gcgcgataaa      60

cgcatccgcc cggatggcaa cgatcagtat attcgcctgg atcatgttga cggttggagc     120

catgaccctt atatgccgat caccccgcgc gagccgaaac tggaccatgt tacatttgca     180

ttcatcggcg gcggttttag cggtctggtg accgccgcac gtctgcgtga aagtggcgtg     240

gagagtgttc gcatcatcga caaagcaggc gatttcggcg gcgtttggta ttggaaccgt     300

tatccgggtg ccatgtgcga taccgcagca atggtgtaca tgcctctgct ggaagagacc     360

ggctacatgc cgacagaaaa atatgctcat ggtccggaga ttctggagca ctgtcagcgc     420

atcggcaaac actacgacct gtatgacgat gccctgttcc ataccgaagt taccgacctg     480

gtgtggcagg agcatgatca gcgttggcgc atcagcacaa accgcggtga ccatttcacc     540

gcacagttcg ttggcatggg taccggcccg ctgcacgttg cacagctgcc gggtattccg     600

ggtatcgaga gcttccgtgg taagagcttc cataccagcc gctgggacta tgactataca     660

ggtggcgacg cactgggcgc acctatggac aaactggcag acaaacgcgt ggcagtgatt     720

ggtaccggcg caaccgccgt tcagtgcgtt ccggaactgg ccaagtactg ccgcgaactg     780

tatgtggttc agcgcacccc gagtgccgtt gatgaacgcg gcaaccatcc gatcgatgaa     840

aagtggttcg cccagattgc cacacctggt tggcagaaac gctggctgga tagctttacc     900

gcaatctggg atggtgtgct gacagatccg agcgaactgg ccatcgagca tgaagacctg     960

gtgcaggatg gttggacagc actgggtcag cgcatgcgtg cagccgtggg tagcgttccg    1020

attgaacagt atagcccgga gaacgtgcag cgtgccctgg aagaggccga cgatgaacag    1080

atggaacgca ttcgcgcacg tgtggatgag attgtgaccg atcctgccac cgccgcccag    1140

ctgaaagcat ggtttcgcca gatgtgcaag cgtccgtgct tccacgatga ctatctgcct    1200

gcattcaacc gcccgaatac ccatctggtg gacacaggtg gcaaaggcgt ggagcgcatt    1260

accgaaaacg gtgtggtggt tgcaggtgtg gaatatgagg tggactgcat cgtgtacgcc    1320

agtggcttcg agttcttagg caccggttat acagaccgtg caggtttcga tccgaccggc    1380

cgtgatggcg ttaaactgag cgaacattgg gcccaaggca cacgtaccct gcatggcatg    1440

catacctacg gctttccgaa cctgtttgtg ctgcagctga tgcagggtgc agccctgggt    1500

agcaacatcc cgcacaactt tgttgaagcc gcccgcgtgg tggccgcaat tgttgatcat    1560

gtgctgagca caggcaccag tagcgttgaa accaccaagg aagccgaaca agcctgggtg    1620

cagctgctgc tggatcacgg tcgccctctg ggcaacccgg agtgtacacc tggttattac    1680

aataatgaag gcaaaccggc cgaactgaag gaccgtctga acgttggcta tccggccggt    1740

agcgccgcct tttttcgtat gatggaccac tggctggcag ccggcagttt tgatggcctg    1800

acattccgct aa                                                        1812
```

MONOOXYGENASE MUTANT AND USE THEREOF

INCORPORATION OF SEQUENCE LISTING

This application contains a sequence listing submitted in Computer Readable Form (CRF). The CFR file containing the sequence listing entitled "PAL2344706_ST25", which was created on Apr. 28, 2021, and is 7,955 bytes in size. The information in the sequence listing is incorporated herein by reference in its entirety.

TECHNICAL FIELD

The disclosure relates to the field of biotechnologies, and in particular to a monooxygenase mutant and use thereof.

BACKGROUND

Chiral sulfoxides widely exist in natural world, and are structural units of many important bioactive molecules, as well as important intermediates for synthesis of natural products and chiral drugs. Many chiral sulfoxides contain one or more chiral centers. Pharmacological activities, metabolic processes, metabolic rates, and toxicities of the different chiral drugs are significantly different. Generally, one enantiomer is effective, while another enantiomer is low-effective or non-effective, even toxic. Therefore, how to construct compounds containing the chiral centers efficiently and stereoselectively has great significance in medical research and development.

Baeyer Villiger monooxygenases (BVMOs) belong to flavin monooxygenases, it is usually used to stereoselectively oxidize chain and cyclic ketones to generate corresponding esters or lactones, and may also catalyze electrophilic oxidation reactions of sulfur, nitrogen and phosphorus. At the same time, the BVMOs may also catalyze the nucleophilic oxidation reactions of ketone and boron. The BVMOs have important applications in the synthesis of the chiral drugs. For example, it may catalyze oxidation of a sulfur-containing chiral precursor, and is used in synthesis of chiral drugs Modafinil and Omeprazole (CN105695425A).

Although several of the BVMOs are commercially applied, the BVMOs generally have problems such as low enzyme activity, low enzyme stability, and generation of a by-product sulfone. Generally speaking, a wild-type enzyme may be transformed by us through means of directed evolution to improve various properties of the enzyme, and thereby it may be used in production (*Chem. Rev.* 2011, 111: 4165-4222).

SUMMARY

The disclosure aims to provide a monooxygenase mutant and use thereof, as to solve technical problems in the prior art that a monooxygenase is low in enzyme activity and a by-product sulfone is higher in content.

In order to achieve the above purpose, according to one aspect of the disclosure, a monooxygenase mutant is provided. An amino acid sequence of the monooxygenase mutant is obtained by mutation of an amino acid sequence shown in SEQ ID NO: 1, and the mutation at least includes one of the following mutation sites: 45-th site, 95-th site, 106-th site, 108-th site, 114-th site, 186-th site, 190-th site, 191-th site, 249-th site, 257-th site, 393-th site, 436-th site, 499-th site, 500-th site, 501-th site, 503-th site, 504-th site, 559-th site, and 560-th site, and the mutation is that a methionine in the 45-th site is mutated into a threonine; an alanine in the 95-th site is mutated into a threonine; a cysteine in the 106-th site is mutated into a serine; a threonine in the 108-th site is mutated into a serine; a methionine in the 114-th site is mutated into a leucine, a methionine in the 186-th site is mutated into an isoleucine, a proline in the 190-th site is mutated into a glutamine, a glycine, an arginine, an asparagine, a glutamic acid, a valine, a threonine, an isoleucine, a histidine, a tyrosine, a phenylalanine or a leucine, a leucine in the 191-th site is mutated into a valine, a cysteine in the 249-th site is mutated into a valine, a cysteine in the 257-th site is mutated into an alanine, a cysteine in the 393-th site is mutated into a valine, a cysteine in the 436-th site is mutated into a serine, a leucine in the 499-th site is mutated into an alanine, a glycine in the 500-th site is mutated into a leucine, a serine in the 501-th site is mutated into a threonine, an isoleucine in the 503-th site is mutated into an alanine, a proline in the 504-th site is mutated into a threonine, a valine or a serine, a tyrosine in the 559-th site is mutated into a phenylalanine, a lysine, a methionine, a proline, a glutamine, an asparagine, a serine, an arginine, a valine, an aspartic acid, an isoleucine, a serine, a leucine or an alanine and a tyrosine in the 560-th site is mutated into a phenylalanine, a leucine, a serine, a proline, a methionine, or a alanine; or the amino acid sequence of the monooxygenase mutant is an amino acid sequence having the mutation sites in the mutated amino acid sequence, and having more than 80% of homology with the mutated amino acid sequence.

Further, the mutation at least includes one of the following mutation site combinations: a tyrosine in the 559-th site is mutated into a lysine and a proline in the 190-th site is mutated into a leucine; a tyrosine in the 559-th site is mutated into a methionine and a proline in the 190-th site is mutated into a leucine; a tyrosine in the 559-th site is mutated into a proline and a proline in the 190-th site is mutated into a leucine; a tyrosine in the 559-th site is mutated into a glutamine and a proline in the 190-th site is mutated into a leucine; a tyrosine in the 559-th site is mutated into a leucine and a proline in the 190-th site is mutated into a leucine; a tyrosine in the 559-th site is mutated into an asparagines and a proline in the 190-th site is mutated into a leucine; a tyrosine in the 559-th site is mutated into a threonine and a proline in the 190-th site is mutated into a leucine; a tyrosine in the 559-th site is mutated into an arginine and a proline in the 190-th site is mutated into a leucine; a tyrosine in the 559-th site is mutated into a valine and a proline in the 190-th site is mutated into a leucine; a tyrosine in the 559-th site is mutated into an aspartic acid and a proline in the 190-th site is mutated into a leucine; a tyrosine in the 559-th site is mutated into an isoleucine and a proline in the 190-th site is mutated into a leucine; a tyrosine in the 559-th site is mutated into an alanine and a proline in the 190-th site is mutated into a leucine; a tyrosine in the 559-th site is mutated into a serine and a proline in the 190-th site is mutated into a leucine; a tyrosine in the 560-th site is mutated into a phenylalanine and a proline in the 190-th site is mutated into a leucine; a tyrosine in the 560-th site is mutated into a leucine and a proline in the 190-th site is mutated into a leucine; a tyrosine in the 560-th site is mutated into a serine and a proline in the 190-th site is mutated into a leucine; a tyrosine in the 560-th site is mutated into a phenylalanine and a proline in the 190-th site is mutated into a glutamine; a tyrosine in the 560-th site is mutated into a phenylalanine and a proline in the 190-th is mutated into a glycine; a tyrosine in the 560-th site is mutated into a phenylalanine and a proline in the 190-th site is mutated into an arginine; a tyrosine in the 560-th site is mutated into a phenylalanine and a proline in the 190-th site is mutated into an asparagine; a tyrosine in the 560-th site is mutated into a phenylalanine and a proline in the 190-th site is mutated into a phenylalanine; a tyrosine in the 560-th site is mutated into a phenylalanine and a proline in the 190-th site is mutated into a glutamic acid; a tyrosine in the 560-th site is mutated into a phenylalanine and a proline in the 190-th site is mutated into a valine; a tyrosine in the 560-th site is mutated into a phenylalanine and a proline in the 190-th site is mutated into a threonine; a tyrosine in the 560-th site is mutated into a phenylalanine and a proline in the 190-th site is mutated into an isoleucine; a tyrosine in the 560-th site is mutated into a phenylalanine and a proline in the 190-th site is mutated into a histidine; a tyrosine in the 560-th site is mutated into a phenylalanine and a proline in the 190-th site is mutated into a tyrosine; a tyrosine in the 560-th site is mutated into a proline and a proline in the 190-th site is mutated into a leucine; a tyrosine in the 559-th site is mutated into an alanine, a tyrosine in the 560-th site is mutated into a methionine and a proline in the 190-th site is mutated into a leucine; a tyrosine in the 559-th site is mutated into an alanine, a tyrosine in the 560-th site is mutated into an phenylalanine and a proline in the 190-th site is mutated into a leucine; a tyrosine in the 559-th site is mutated into an alanine, a tyrosine in the 560-th site is mutated into a leucine and a proline in the 190-th site is mutated into a leucine; a tyrosine in the 559-th site is mutated into a phenylalanine, a tyrosine in the 560-th site is mutated into a phenylalanine and a proline in the 190-th site is mutated into a leucine; a tyrosine in the 559-th site is mutated into a phenylalanine, a tyrosine in the 560-th site is mutated into a leucine and a proline in the 190-th is mutated into a leucine; a tyrosine in the 559-th site is mutated into a histidine, a tyrosine in the 560-th site is mutated into a leucine and a proline in the 190-th site is mutated into a leucine; a tyrosine in the 559-th site is mutated into a lysine, a tyrosine in the 560-th site is mutated into a leucine and a proline in the 190-th site is mutated into a leucine; a tyrosine in the 559-th site is mutated into a leucine, a tyrosine in the 560-th site is mutated into a phenylalanine and a proline in the 190-th site is mutated into a leucine; a tyrosine in the 559-th site is mutated into a leucine, a tyrosine in the 560-th site is mutated into a leucine and a proline in the 190-th site is mutated into a leucine; a tyrosine in the 559-th site is mutated into a glutamine, a tyrosine in the 560-th site is mutated into a phenylalanine and a proline in the 190-th site is mutated into a leucine; a tyrosine in the 559-th site is mutated into a methionine, a tyrosine in the 560-th site is mutated into a phenylalanine and a proline in the 190-th site is mutated into a leucine; a tyrosine in the 559-th site is mutated into an asparagine, a tyrosine in the 560-th site is mutated into a leucine and a proline in the 190-th site is mutated into a leucine; a tyrosine in the 559-th site is mutated into a proline, a tyrosine in the 560-th site is mutated into a leucine and a proline in the 190-th site is mutated into a leucine; a tyrosine in the 559-th site is mutated into a glutamine, a tyrosine in the 560-th site is mutated into a leucine and a proline in the 190-th site is mutated into a leucine; a tyrosine in the 559-th site is mutated into a serine, a tyrosine in the 560-th site is mutated into a phenylalanine and a proline in the 190-th site is mutated into a leucine; a tyrosine in the 559-th site is mutated into a serine, a tyrosine in the 560-th site is mutated into a leucine and a proline in the 190-th site is mutated into a leucine; a tyrosine in the 559-th site is mutated into a serine, a tyrosine in the 560-th site is mutated into a proline and a proline in the 190-th site is mutated into a leucine; a tyrosine in the 559-th site is mutated into a threonine, a tyrosine in the 560-th site is mutated into a phenylalanine and a proline in the 190-th site is mutated into a leucine; a tyrosine in the 559-th site is mutated into a threonine, a tyrosine in the 560-th site is mutated into a glycine and a proline in the 190-th site is mutated into a leucine; a tyrosine in the 559-th site is mutated into a threonine, a tyrosine in the 560-th site is mutated into a leucine and a proline in the 190-th site is mutated into a leucine; a tyrosine in the 559-th site is mutated into a valine, a tyrosine in the 560-th site is mutated into an alanine and a proline in the 190-th site is mutated into a leucine; a tyrosine in the 559-th site is mutated into a valine, a tyrosine in the 560-th site is mutated into a phenylalanine and a proline in the 190-th site is mutated into a leucine; a tyrosine in the 559-th site is mutated into a valine, a tyrosine in the 560-th site is mutated into a leucine and a proline in the 190-th site is mutated into a leucine; a tyrosine in the 559-th site is mutated into a valine, a tyrosine in the 560-th site is mutated into a glutamine and a proline in the 190-th site is mutated into a leucine; a tyrosine in the 559-th site is mutated into a methionine, a proline in the 504-th site is mutated into an alanine and a proline in the 190-th site is mutated into a leucine; a tyrosine in the 559-th site is mutated into a methionine, a proline in the 504-th site is mutated into an isoleucine and a proline in the 190-th site is mutated into a leucine; a tyrosine in the 559-th site is mutated into a methionine, an asparagines in the 503-th site is mutated into a valine and a proline in the 190-th site is mutated into a leucine; a tyrosine in the 559-th site is mutated into a methionine, a proline in the 504-th site is mutated into a threonine and a proline in the 190-th site is mutated into a leucine; a tyrosine in the 559-th site is mutated into a methionine, a proline in the 504-th site is mutated into a valine and a proline in the 190-th site is mutated into a leucine; a tyrosine in the 559-th site is mutated into a methionine, a proline in the 504-th site is mutated into a serine and a proline in the 190-th site is mutated into a leucine; and preferably, the mutation at least includes one of the following mutation site combinations: a proline in the 190-th site is mutated into a leucine, a tyrosine in the 559-th site is mutated into a methionine and a methionine in the 45-th site mutated into a threonine; a proline in the 190-th site is mutated into a leucine, a tyrosine in the 559-th site is mutated into a methionine and a cysteine in the 257-th site is mutated into an alanine; a proline in the 190-th site is mutated into a leucine, a tyrosine in the 559-th site is mutated into a methionine and a cysteine in the 249-th site is mutated into a valine; a proline in the 190-th site is mutated into a leucine, a tyrosine in the 559-th site is mutated into a methionine and a cysteine in the 393-th site is mutated into a valine; a proline in the 190-th site is mutated into a leucine, a tyrosine in the 559-th site is mutated into a methionine and a methionine in the 186-th site is mutated into an isoleucine; a proline in the 190-th site is mutated into a leucine, a tyrosine in the 559-th site is mutated into a methionine, a cysteine in the 249-th site is mutated into a valine and a cysteine in the 393-th site is mutated into a valine; a proline in the 190-th site is mutated into a leucine, a tyrosine in the 559-th site is mutated into a methionine, a cysteine in the 249-th site is mutated into a valine, a cysteine in the 393-th site is mutated into a valine and a cysteine in the 257-th site is mutated into an alanine;

a proline in the 190-th site is mutated into a leucine, a tyrosine in the 559-th site is mutated into a methionine, a cysteine in the 249-th site is mutated into a valine, a cysteine in the 393-th site is mutated into a valine, a cysteine in the 257-th site is mutated into an alanine and a methionine in the 45-th site is mutated into a threonine; a proline in the 190-th site is mutated into a leucine, a tyrosine in the 559-th site is mutated into a methionine, a cysteine in the 249-th site is mutated into a valine, a cysteine in the 393-th site is mutated into a valine, a cysteine in the 257-th site is mutated into an alanine, a methionine in the 45-th site is mutated into a threonine and a methionine in the 186-th site is mutated into an isoleucine. According to another aspect of the disclosure, a DNA molecule is provided. The DNA molecule encodes the above monooxygenase mutant.

According to another aspect of the disclosure, a recombinant plasmid is provided. The recombinant plasmid contains the above DNA molecule.

Further, the recombinant plasmid is pET-22b(+), pET-22b (+), pET-3a(+), pET-3d(+), pET-11a(+), pET-12a(+), pET-14b(+), pET-15b(+), pET-16b(+), pET-17b(+), pET-19b(+), pET-20b(+), pET-21a(+), pET-23a(+), pET-23b(+), pET-24a (+), pET-25b(+), pET-26b(+), pET-27b(+), pET-28a(+), pET-29a(+), pET-30a(+), pET-31b(+), pET-32a(+), pET-35b (+), pET-38b(+), pET-39b(+), pET-40b(+), PET-41a(+), pET-41b(+), pET-42a(+), pET-43a(+), pET-43b(+), pET-44a (+), pET-49b(+), pQE2, pQE9, pQE30, pQE31, pQE32, pQE40, pQE70, pQE80, pRSET-A, pRSET-B, pRSET-C, pGEX-5X-1, pGEX-6p-1, pGEX-6p-2, pBV220, pBV221, pBV222, pTrc99A, pTwin1, pEZZ18, pKK232-18, pUC-18 or pUC-19.

According to another aspect of the disclosure, a host cell is provided. The host cell contains the above recombinant plasmid.

Further, the host cell includes a prokaryotic cell, a yeast or a eukaryotic cell; and preferably, the prokaryotic cell is an *E. coli* BL21 cell or an *E. coli* DH5α competent cell.

According to another aspect of the disclosure, a method for producing a chiral sulfoxide is provided. The method includes a step of performing a catalytic monooxygenation reaction on a thioether compound by a monooxygenase, and the monooxygenase is the above monooxygenase mutant.

Further, the thioether compound is

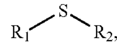

herein $R_1$ and $R_2$ are each independently a $C_1$~$C_8$ alkyl, a $C_5$~$C_{10}$ cycloalkyl, a $C_5$~$C_{10}$ aryl or a $C_5$~$C_{10}$ heteroaryl, or the $R_1$ and $R_2$ together with a carbon on a carbonyl group form a $C_5$~$C_{10}$ heterocyclic group, a $C_5$~$C_{10}$ carbocyclic group or a $C_5$~$C_{10}$ heteroaryl, heteroatoms in the $C_5$~$C_{10}$ heterocyclic group and $C_5$~$C_{10}$ heteroaryl are each independently selected from at least one of nitrogen, oxygen and sulfur, and an aryl in the $C_5$~$C_{10}$ aryl, a heteroaryl in the $C_5$~$C_{10}$ heteroaryl, a carbocyclic group in the $C_5$~$C_{10}$ carbocyclic group or a heterocyclic group in the $C_5$~$C_{10}$ heterocyclic group is each independently unsubstituted or substituted with at least one group of a halogen, an alkoxy or an alkyl.

Further, the thioether compound is

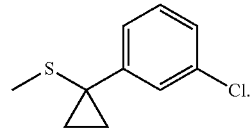

Further, the monooxygenase is cell lysate enzyme solution, a whole cell, freeze-dried enzyme powder, a freeze-dried cell, an immobilized enzyme or an immobilized cell of the monooxygenase mutant.

Further, a reaction system of the monooxygenation reaction further includes a cofactor, the cofactor is NAD/NADH and/or NADP/NADPH, and a cofactor circulation system includes glucose and glucose dehydrogenase, formate and formate dehydrogenase, glucose 6-phosphate and glucose-6-phosphate dehydrogenase, or secondary alcohol and secondary alcohol dehydrogenase.

Further, an addition amount of the monooxygenase in the reaction system of the monooxygenation reaction is 0.1 to 10 times of a substrate mass.

Further, a temperature of the monooxygenation reaction is 10~50° C., preferably 30° C.

Further, the monooxygenation reaction is performed at a pH of 7~10, preferably a pH of 9. The monooxygenase mutant of the disclosure is based on the monooxygenase shown in the SEQ ID NO: 1, and mutated through a method of site-directed mutagenesis, thereby the amino acid sequence thereof is changed to achieve changes in protein structure and function, and the monooxygenase with the above mutation sites is obtained by a method of directional screening. The monooxygenase mutant of the disclosure has an advantage of greatly improving the enzyme activity, thereby a cost in industrial production of the chiral sulfoxide is greatly reduced.

DETAILED DESCRIPTION OF THE EMBODIMENTS

It is to be noted that embodiments in the present application and features in the embodiments may be combined with each other in the case without conflicting. The disclosure is described in detail below in combination with the embodiments.

A monooxygenase derived from *Brachymonas petroleovorans* may catalyze conversion of (3-chlorobenzyl) dimethyl sulfide high-selectively. However, for conversion of (1-(3-chlorophenyl)cyclopropyl)methyl sulfide, an ee value of a catalytic product of the monooxygenase derived from the *Brachymonas petroleovorans* is only 43.9%. After screening other monooxygenases, it is discovered that the monooxygenase BVMO derived from *Rhodococcus ruber*-SD1 may catalyze the conversion of the substrate (1-(3-chlorophenyl)cyclopropyl) methyl sulfide with higher selectivity. The ee value is 99%, but the activity thereof is lower, a by-product sulfone (peroxide) after a reaction is larger in content, an amount of an added enzyme during the reaction is larger, and separation and extraction of a product are difficult. The inventor of the disclosure aims to improve the activity of the BVMO, reduce the amount of the used enzyme, improve the selectivity of the enzyme, and reduce the content of the by-product sulfone through a method of directed evolution.

The inventor of the disclosure improves the activity and selectivity of the monooxygenase SEQ ID NO: 1 (MTTSI-DREALRRKYAEER-DKRIRPDGNDQYIRLDHVDGWSHDPYMPIT-PREPKLDHVTFA FIGGGFSGLVTAARLRESGVESVRIIDK-AGDFGGVWYWNRYPGAMCDTAAMVYMPLLEET GYMPTEKYAHGPEILEHCQRIGKHYDLYDD-ALFHTEVTDLVWQEHDQRWRISTNRGDHFT AQFVGMGTGPLHVAQLP-GIPGIESFRGKSFHTSRWDYDYTGGDAL-GAPMDKLADKRVAVI GTGATAVQCVPELAKYCRE-LYVVQRTPSAVDERGNHPIDEKWFAQIATPGWQKRWL-DSFT AIWDGVLTDPSELAIEHEDLVQDGWTALGQRM-RAAVGSVPIEQYSPENVQRALEEADDEQ MERIRARV-DEIVTDPATAAQLKAWFRQMCKRPCFHD-DYLPAFNRPNTHLVDTGGKGVERIT ENGVVVAGVEYEVDCIVYASGFEFLGTGYTDRAG-FDPTGRDGVKLSEHWAQGTRTLHGM HTYGFPNLFVLQLMQGAALG-SNIPNFVEAARVVAAIVDHVLSTGTSSVETTKE-AEQAWV QLLLDHGRPLGNPECTPGYYNNEGKPAEL-KDRLNVGYPAGSAAFFRMMDHWLAAGSFD GLTFR) and a corresponding base sequence SEQ ID NO: 2 (atgacaaccagtatc-gatcgcgaggccctgcgccgcaaatatgccgaagagcgcgataaacg-catccgcccggatggca acgatcagtatattcgcctggatcatgttgacggttg-gagccatgacccttatatgccgatcaccccgcgcgagccgaaactgg accatgttacatttgcattcatcggcggcggttt-tagcggtctggtgaccgccgcacgtctgcgtgaaagtggcgtggagagtgtt cgcatcatcgacaaagcaggcgatttcggcggcgtttggtattggaaccgt-tatccgggtgccatgtgcgataccgcagcaatg gtgtacatgcctctgctg-gaagagaccggctacatgccgacagaaaaatatgctcatggtccggagattctg-gagcactgtca gcgcatcggcaaacactacgacctgtatgacgatgccctgttccataccgaagt-taccgacctggtgtggcaggagcatgatc agcgttggcg-catcagcacaaaccgcggtgaccatttcaccgcacagttcgttgg-catgggtaccggcccgctgcacgttgca cagctgccgggtattccgggtatcgagagcttccgtggtaagagcttccat-accagccgctgggactatgactatacaggtggc gacgcactgggcgcacc-tatggacaaactggcagacaaacgcgtggcagtgat-tggtaccggcgcaaccgccgttcagtgc gttccggaactggc-caagtactgccgcgaactgtatgtggttcagcgcaccccgagtgccgttgat-gaacgcggcaaccatcc gatcgatgaaaagtggttcgcccagattgc-cacacctggttggcagaaacgctggctggatagctttaccgcaatctgggatgg tgtgctgacagatccgagcgaactggccatcgagcatgaagacctggtgcag-gatggttggacagcactgggtcagcgcatg cgtgcagccgtgggtagcgttcc-gattgaacagtatagcccggagaacgtgcagcgtgccctggaagaggccgac-gatgaa cagatggaacgcattcgcgcacgtgtggatgagattgtgaccgatcctgc-caccgccgcccagctgaaagcatggtttcgcca gatgtgcaagcgtccgtgcttc-cacgatgactatctgcctgcattcaaccgcccgaatacc-catctggtggacacaggtggcaa aggcgtggagcgcattaccgaaaacggtgtggtggttgcaggtgtggaatat-gaggtggactgcatcgtgtacgccagtggctt cgagttcttaggcaccggttata-cagaccgtgcaggtttcgatccgaccggccgtgatggcgttaaactgagcgaa-cattgggc ccaaggcacacgtaccctgcatggcatgcatacc-tacggctttccgaacctgtttgtgctgcagctgatgcagggtgcagccctg ggtagcaacatcccgcacaactttgttgaagccgcccgcgtggtggccgcaat-tgttgatcatgtgctgagcacaggcaccagt agcgttgaaaccac-caaggaagccgaacaagcctgggtgcagctgctgctggat-cacggtcgccctctgggcaacccgga gtgtacacctggttattacaataatgaaggcaaaccggccgaact-gaaggaccgtctgaacgttggctatccggccggtagcg ccgcctttttcgtat-gatggaccactggctggcagccggcagttttgatggcctgacattccgctaa), reduces the amount of the used enzyme, and reduces the content of the by-product sulfone through the method of directed evolution. Firstly, a mutation site is introduced into the monooxygenase SEQ ID NO: 1 in a mode of a whole plasmid PCR, and the activity of mutants and the content of the by-product sulfone are detected, the mutants with the improved activity or reduced by-product sulfone content are selected.

The BVMO is used as a template, 34 pairs of site-directed mutagenesis primers are designed (M45T, V95I, C106S, D107A, T108I, T108S, M114L, M186I, P190F, P190L, L191V, L191A, C249V, C257A, C393V, C436S, L499A, L499G, G500L, S501T, N502Q, I503G, I503A, I503M, P504F, G558V, G558N, Y559F, Y559L, Y559A, Y560F, Y560L, Y560A, C555S). A method of the site-directed mutagenesis is used, and pET-28b(+) is used as an expression vector, to obtain a mutant plasmid with a target gene.

Herein, site-directed mutagenesis: refers to introduction of desired changes (usually changes represented in favorable directions) in a target DNA fragment (may be a genome, and may also be a plasmid) through methods such as a polymerase chain reaction (PCR), including addition, deletion, point mutation and the like of a base. The site-directed mutagenesis may quickly and efficiently improve characters and representation of a target protein expressed by a DNA, and it is a very useful method in gene research work.

The method of introducing the site-directed mutagenesis using the whole plasmid PCR is simple and effective, and is a more commonly used method at present. A principle thereof is that a pair of primers (forward and reverse) containing mutation sites are annealed with the template plasmid, and then "circularly extended" by a polymerase. The so-called circular extension means that the polymerase extends the primers according to the template, returns to a 5'-end of the primers for termination after one circle, and then undergoes repeated heating and annealing extension cycles. This reaction is different from rolling circle amplification and may not form multiple tandem copies. Extension products of the forward and reverse primers are annealed and paired to form an open-circle plasmid with a nick. An extension product of Dpn I digestion, because the original template plasmid is derived from conventional *E. coli*, is modified by dam methylation, and is chopped because it is sensitive to Dpn I, but a plasmid with a mutation sequence synthesized in vitro is not digested because there is no methylation, so it is successfully transformed in the subsequent transformation, and a clone of the mutant plasmid may be obtained.

The mutant plasmid obtained above is transformed into *E. coli* cells, and overexpressed in *E. coli*. Then, a crude enzyme is obtained by ultrasonically breaking the cells. The best conditions for inducing expression of an amino acid dehydrogenase: 25° C., inducing with 0.1 mM IPTG overnight.

According to a typical implementation mode of the disclosure, a monooxygenase mutant is provided. An amino acid sequence of the monooxygenase mutant is obtained by mutation of an amino acid sequence shown in SEQ ID NO: 1, and the mutation at least includes one of the following mutation sites: 45-th site, 95-th site, 106-th site, 108-th site, 114-th site, 186-th site, 190-th site, 191-th site, 249-th site, 257-th site, 393-th site, 436-th site, 499-th site, 500-th site, 501-th site, 503-th site, 504-th site, 559-th site, and 560-th site, and the mutation is that a methionine in the 45-th site is mutated into a threonine; an alanine in the 95-th site is mutated into a threonine; a cysteine in the 106-th site is mutated into a serine; a threonine in the 108-th site is mutated into a serine; a methionine in the 114-th site is mutated into a leucine, a methionine in the 186-th site is mutated into an isoleucine, a proline in the 190-th site is mutated into a glutamine, a glycine, an arginine, an asparagine, a glutamic acid, a valine, a threonine, an isoleucine, a histidine, a tyrosine, a phenylalanine or a leucine, a leucine in the 191-th site is mutated into a valine, a cysteine in the 249-th site is mutated into a valine, a cysteine in the 257-th site is mutated into an alanine, a cysteine in the 393-th site is mutated into a valine, a cysteine in the 436-th site is mutated into a serine, a leucine in the 499-th site is mutated into an alanine, a glycine in the 500-th site is mutated into a leucine, a serine in the 501-th site is mutated into a threonine, an isoleucine in the 503-th site is mutated into an alanine, a proline in the 504-th site is mutated into a threonine, a valine or a serine, a tyrosine in the 559-th site is mutated into a phenylalanine, a lysine, a methionine, a proline, a glutamine, an asparagine, a serine, an arginine, a valine, an aspartic acid, an isoleucine, a serine, a leucine or an alanine and a tyrosine in the 560-th site is mutated into a phenylalanine, a leucine, a serine, a proline, a methionine, or a alanine; or the amino acid sequence of the monooxygenase mutant is an amino acid sequence having the mutation sites in the mutated amino acid sequence, and having more than 80% of homology with the mutated amino acid sequence.

Preferably, the mutation at least includes one of the following mutation site combinations: a tyrosine in the 559-th site is mutated into a lysine and a proline in the 190-th site is mutated into a leucine; a tyrosine in the 559-th site is mutated into a methionine and a proline in the 190-th site is mutated into a leucine; a tyrosine in the 559-th site is mutated into a proline and a proline in the 190-th site is mutated into a leucine; a tyrosine in the 559-th site is mutated into a glutamine and a proline in the 190-th site is mutated into a leucine; a tyrosine in the 559-th site is mutated into a leucine and a proline in the 190-th site is mutated into a leucine; a tyrosine in the 559-th site is mutated into an asparagines and a proline in the 190-th site is mutated into a leucine; a tyrosine in the 559-th site is mutated into a threonine and a proline in the 190-th site is mutated into a leucine; a tyrosine in the 559-th site is mutated into an arginine and a proline in the 190-th site is mutated into a leucine; a tyrosine in the 559-th site is mutated into a valine and a proline in the 190-th site is mutated into a leucine; a tyrosine in the 559-th site is mutated into an aspartic acid and a proline in the 190-th site is mutated into a leucine; a tyrosine in the 559-th site is mutated into an isoleucine and a proline in the 190-th site is mutated into a leucine; a tyrosine in the 559-th site is mutated into an alanine and a proline in the 190-th site is mutated into a leucine; a tyrosine in the 559-th site is mutated into a serine and a proline in the 190-th site is mutated into a leucine; a tyrosine in the 560-th site is mutated into a phenylalanine and a proline in the 190-th site is mutated into a leucine; a tyrosine in the 560-th site is mutated into a leucine and a proline in the 190-th site is mutated into a leucine; a tyrosine in the 560-th site is mutated into a serine and a proline in the 190-th site is mutated into a leucine; a tyrosine in the 560-th site is mutated into a phenylalanine and a proline in the 190-th site is mutated into a glutamine; a tyrosine in the 560-th site is mutated into a phenylalanine and a proline in the 190-th is mutated into a glycine; a tyrosine in the 560-th site is mutated into a phenylalanine and a proline in the 190-th site is mutated into an arginine; a tyrosine in the 560-th site is mutated into a phenylalanine and a proline in the 190-th site is mutated into an asparagine; a tyrosine in the 560-th site is mutated into a phenylalanine and a proline in the 190-th site is mutated into a phenylalanine; a tyrosine in the 560-th site is mutated into a phenylalanine and a proline in the 190-th site is mutated into a glutamic acid; a tyrosine in the 560-th site is mutated into a phenylalanine and a proline in the 190-th site is mutated into a valine; a tyrosine in the 560-th site is mutated into a phenylalanine and a proline in the 190-th site is mutated into a threonine; a tyrosine in the 560-th site is mutated into a phenylalanine and a proline in the 190-th site is mutated into an isoleucine; a tyrosine in the 560-th site is mutated into a phenylalanine and a proline in the 190-th site is mutated into a histidine; a tyrosine in the 560-th site is mutated into a phenylalanine and a proline in the 190-th site is mutated into a tyrosine; a tyrosine in the 560-th site is mutated into a proline and a proline in the 190-th site is mutated into a leucine; a tyrosine in the 559-th site is mutated into an alanine, a tyrosine in the 560-th site is mutated into a methionine and a proline in the 190-th site is mutated into a leucine; a tyrosine in the 559-th site is mutated into an alanine, a tyrosine in the 560-th site is mutated into an phenylalanine and a proline in the 190-th site is mutated into a leucine; a tyrosine in the 559-th site is mutated into an alanine, a tyrosine in the 560-th site is mutated into a leucine and a proline in the 190-th site is mutated into a leucine; a tyrosine in the 559-th site is mutated into a phenylalanine, a tyrosine in the 560-th site is mutated into a phenylalanine and a proline in the 190-th site is mutated into a leucine; a tyrosine in the 559-th site is mutated into a phenylalanine, a tyrosine in the 560-th site is mutated into a leucine and a proline in the 190-th is mutated into a leucine; a tyrosine in the 559-th site is mutated into a histidine, a tyrosine in the 560-th site is mutated into a leucine and a proline in the 190-th site is mutated into a leucine; a tyrosine in the 559-th site is mutated into a lysine, a tyrosine in the 560-th site is mutated into a leucine and a proline in the 190-th site is mutated into a leucine; a tyrosine in the 559-th site is mutated into a leucine, a tyrosine in the 560-th site is mutated into a phenylalanine and a proline in the 190-th site is mutated into a leucine; a tyrosine in the 559-th site is mutated into a leucine, a tyrosine in the 560-th site is mutated into a leucine and a proline in the 190-th site is mutated into a leucine; a tyrosine in the 559-th site is mutated into a glutamine, a tyrosine in the 560-th site is mutated into a phenylalanine and a proline in the 190-th site is mutated into a leucine; a tyrosine in the 559-th site is mutated into a methionine, a tyrosine in the 560-th site is mutated into a phenylalanine and a proline in the 190-th site is mutated into a leucine; a tyrosine in the 559-th site is mutated into an asparagine, a tyrosine in the 560-th site is mutated into a leucine and a proline in the 190-th site is mutated into a leucine; a tyrosine in the 559-th site is mutated into a proline, a tyrosine in the 560-th site is mutated into a leucine and a proline in the 190-th site is mutated into a leucine; a tyrosine in the 559-th site is mutated into a glutamine, a tyrosine in the 560-th site is mutated into a leucine and a proline in the 190-th site is mutated into a leucine; a tyrosine in the 559-th site is mutated into a serine, a tyrosine in the 560-th site is mutated into a phenylalanine and a proline in the 190-th site is mutated into a leucine; a tyrosine in the 559-th site is mutated into a serine, a tyrosine in the 560-th site is mutated into a leucine and a proline in the 190-th site is mutated into a leucine; a tyrosine in the 559-th site is mutated into a serine, a tyrosine in the 560-th site is mutated into a proline and a proline in the 190-th site is mutated into a leucine; a tyrosine in the 559-th site is mutated into a threonine, a tyrosine in the 560-th site is mutated into a phenylalanine and a proline in the 190-th site is mutated into a leucine; a tyrosine in the 559-th site is mutated into a threonine, a tyrosine in the 560-th site is mutated into a glycine and a proline in the 190-th site is mutated into a leucine; a tyrosine in the 559-th site is mutated into a threonine, a tyrosine in the 560-th site is mutated into a leucine and a proline in the 190-th site is mutated into a leucine; a tyrosine in the 559-th site is mutated into a valine, a tyrosine in the 560-th site is mutated into an alanine and a proline in the 190-th site is mutated into a leucine; a tyrosine in the 559-th site is mutated into a valine, a tyrosine in the 560-th site is mutated into a phenylalanine and a proline in the 190-th site is mutated into a leucine; a tyrosine in the 559-th site is mutated into a valine, a tyrosine in the 560-th site is mutated into a leucine and a proline in the 190-th site is mutated into a leucine; a tyrosine in the 559-th site is mutated into a valine, a tyrosine in the 560-th site is mutated into a glutamine and a proline in the 190-th site is mutated into a leucine; a tyrosine in the 559-th site is mutated into a methionine, a proline in the 504-th site is mutated into an alanine and a proline in the 190-th site is mutated into a leucine; a tyrosine in the 559-th site is mutated into a methionine, a proline in the 504-th site is mutated into an isoleucine and a proline in the 190-th site is mutated into a leucine; a tyrosine in the 559-th site is mutated into a methionine, an asparagines in the 503-th site is mutated into a valine and a proline in the 190-th site is mutated into a leucine; a tyrosine in the 559-th site is mutated into a methionine, a proline in the 504-th site is mutated into a threonine and a proline in the 190-th site is mutated into a leucine; a tyrosine in the 559-th site is mutated into a methionine, a proline in the 504-th site is mutated into a valine and a proline in the 190-th site is mutated into a leucine; a tyrosine in the 559-th site is mutated into a methionine, a proline in the 504-th site is mutated into a serine and a proline in the 190-th site is mutated into a leucine. Preferably, the mutation at least includes one of the following mutation site combinations: a proline in the 190-th site is mutated into a leucine, a tyrosine in the 559-th site is mutated into a methionine and a methionine in the 45-th site mutated into a threonine; a proline in the 190-th site is mutated into a leucine, a tyrosine in the 559-th site is mutated into a methionine and a cysteine in the 257-th site is mutated into an alanine; a proline in the 190-th site is mutated into a leucine, a tyrosine in the 559-th site is mutated into a methionine and a cysteine in the 249-th site is mutated into a valine; a proline in the 190-th site is mutated into a leucine, a tyrosine in the 559-th site is mutated into a methionine and a cysteine in the 393-th site is mutated into a valine; a proline in the 190-th site is mutated into a leucine, a tyrosine in the 559-th site is mutated into a methionine and a methionine in the 186-th site is mutated into an isoleucine; a proline in the 190-th site is mutated into a leucine, a tyrosine in the 559-th site is mutated into a methionine, a cysteine in the 249-th site is mutated into a valine and a cysteine in the 393-th site is mutated into a valine; a proline in the 190-th site is mutated into a leucine, a tyrosine in the 559-th site is mutated into a methionine, a cysteine in the 249-th site is mutated into a valine, a cysteine in the 393-th site is mutated into a valine and a cysteine in the 257-th site is mutated into an alanine; a proline in the 190-th site is mutated into a leucine, a tyrosine in the 559-th site is mutated into a methionine, a cysteine in the 249-th site is mutated into a valine, a cysteine in the 393-th site is mutated into a valine, a cysteine in the 257-th site is mutated into an alanine and a methionine in the 45-th site is mutated into a threonine; a proline in the 190-th site is mutated into a leucine, a tyrosine in the 559-th site is mutated into a methionine, a cysteine in the 249-th site is mutated into a valine, a cysteine in the 393-th site is mutated into a valine, a cysteine in the 257-th site is mutated into an alanine, a methionine in the 45-th site is mutated into a threonine and a methionine in the 186-th site is mutated into an isoleucine. The monooxygenase mutant of the disclosure is based on the monooxygenase shown in the SEQ ID NO: 1, and mutated through a method of site-directed mutagenesis, thereby the amino acid sequence thereof is changed to achieve changes in protein structure and function, and the monooxygenase with the above mutation sites is obtained by a method of directional screening. The monooxygenase mutant of the disclosure has an advantage of greatly improving the enzyme activity, and the selectivity of the enzyme is greatly improved, and the by-product sulfone content is greatly reduced, thereby a cost in industrial production of the chiral sulfoxide is greatly reduced.

According to a typical implementation mode of the disclosure, a DNA molecule is provided. The DNA molecule encodes the above monooxygenase mutant. The monooxygenase obtained by the above DNA encoding improves the enzyme activity and the enzyme selectivity, reduces the content of the by-product sulfone, reduces the amount of the added enzyme in industrial production of a chiral sulfoxide, and reduces the difficulty of post-treatment separation and purification.

The above DNA molecule of the disclosure may also exist in the form of an "expression cassette". The "expression cassette" refers to a linear or circular nucleic acid molecule, including DNA and RNA sequences that may direct the expression of a specific nucleotide sequence in an appropriate host cell. Generally speaking, it includes a promoter operatively linked with a target nucleotide, and optionally it is operatively linked with a termination signal and/or other regulatory elements. The expression cassette may also include sequences required for proper translation of the nucleotide sequence. An encoding region usually encodes the target protein, but also encodes a target functional RNA in a sense or antisense direction, such as an antisense RNA or an untranslated RNA. The expression cassette containing a target polynucleotide sequence may be chimeric, it means that at least one of components thereof is heterologous to at least one of the other components thereof. The expression cassette may also naturally exist, but is obtained by efficient recombination for heterologous expression.

According to a typical implementation mode of the disclosure, a recombinant plasmid is provided. The recombinant plasmid contains any one of the above DNA molecules. The DNA molecule in the above recombinant plasmid is placed in a suitable position of the recombinant plasmid, so that the above DNA molecule may be replicated, transcripted or expressed correctly and smoothly.

Although a qualifier used in the disclosure to define the above DNA molecule is "containing", it does not mean that other sequences which are not related to a function thereof may be arbitrarily added to both ends of the DNA sequence. It is known by those skilled in the art that in order to meet requirements of a recombination operation, it is necessary to add appropriate restriction endonuclease digestion sites at both ends of the DNA sequence, or add additional a start codon, a stop codon and the like. Therefore, if a closed expression is used to limit, these situations may not be truly covered.

A term "plasmid" used in the disclosure includes any plasmids, cosmids, bacteriophages or agrobacterium binary nucleic acid molecules in double-stranded or single-stranded linear or circular form, preferably a recombinant expression plasmid, it may be a prokaryotic expression plasmid, and may also be a eukaryotic expression plasmid, but preferably the prokaryotic expression plasmid. In some implementation schemes, the recombinant plasmid is selected from pET-22b (+), pET-22b(+), pET-3a(+), pET-3d(+)), pET-11a(+), pET-12a(+), pET-14b(+), pET-15b(+), pET-16b(+), pET-17b(+), pET-19b(+), PET-20b(+), pET-21a(+), pET-23a(+), pET-23b (+), pET-24a(+), pET-25b(+), pET-26b(+), pET-27b(+), pET-28a(+), pET-29a(+), pET-30a(+), pET-31b(+), pET-32a (+), pET-35b(+), pET-38b(+), pET-39b(+), pET-40b(+), pET-41a(+), pET-41b(+), pET-42a(+), pET-43a(+), pET-43b (+), pET-44a(+), pET-49b(+), pQE2, pQE9, pQE30, pQE31, pQE32, pQE40, pQE70, pQE80, pRSET-A, pRSET-B, pRSET-C, pGEX-5X-1, pGEX-6p-1, pGEX-6p-2, pBV220, pBV221, pBV222, pTrc99A, pTwin1, pEZZ18, pKK232-18, pUC-18 or pUC-19. More preferably, the above recombinant plasmid is pET-22b(+).

According to a typical implementation mode of the disclosure, a host cell is provided. The host cell contains any one of the above recombinant plasmids. The host cell suitable for the disclosure includes but is not limited to a prokaryotic cell, a yeast or a eukaryotic cell. Preferably, the prokaryotic cell is eubacteria, for example, gram-negative bacteria or gram-positive bacteria. More preferably, the prokaryotic cell is an *E. coli* BL21 cell or an *E. coli* DH5α competent cell. The best conditions for inducing the expression of the monooxygenase: 25° C., inducing with 0.1 mM IPTG for 16 h. The mutant plasmid is transformed into the *E. coli* cells, and then a crude enzyme is obtained by a method of ultrasonically breaking the cells.

According to a typical implementation mode of the disclosure, a method for producing a chiral sulfoxide is provided. The method includes a step of performing a catalytic monooxygenation reaction on a thioether compound by a monooxygenase, herein the monooxygenase is any one of the above monooxygenase mutants. Because the above monooxygenase mutant of the disclosure has higher enzyme catalytic activity and higher selectivity, the chiral sulfoxide prepared by using the monooxygenase mutant of the disclosure may not only reduce the production cost, but also an ee value of the obtained chiral sulfoxide is greater than 99%, and a de value is greater than 99%.

In a typical implementation mode of the disclosure the thioether compound is

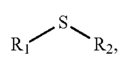

herein $R_1$ and $R_2$ are each independently a $C_1$~$C_8$ alkyl, a $C_5$~$C_{10}$ cycloalkyl, a $C_5$~$C_{10}$ aryl or a $C_5$~$C_{10}$ heteroaryl, or the $R_1$ and $R_2$ together with a carbon on a carbonyl group form a $C_5$~$C_{10}$ heterocyclic group, a $C_5$~$C_{10}$ carbocyclic group or a $C_5$~$C_{10}$ heteroaryl, heteroatoms in the $C_5$~$C_{10}$ heterocyclic group and $C_5$~$C_{10}$ heteroaryl are each independently selected from at least one of nitrogen, oxygen and sulfur, and an aryl in the $C_5$~$C_{10}$ aryl, a heteroaryl in the $C_5$~$C_{10}$ heteroaryl, a carbocyclic group in the $C_5$~$C_{10}$ carbocyclic group or a heterocyclic group in the $C_5$~$C_{10}$ heterocyclic group is each independently unsubstituted or substituted with at least one group of a halogen, an alkoxy or an alkyl.

Typically,

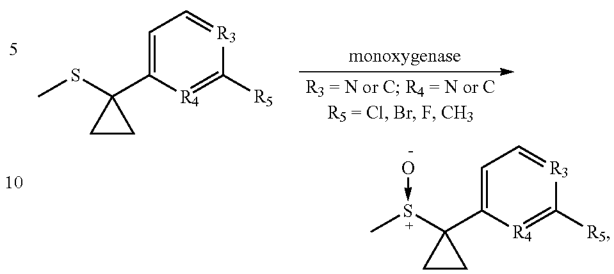

the thioether compound is

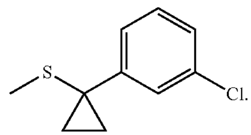

(1-(3-chlorophenyl)cyclopropyl)methyl sulfide).

The monooxygenase may be cell lysate enzyme solution, a whole cell, freeze-dried enzyme powder, a freeze-dried cell, an immobilized enzyme or an immobilized cell of the monooxygenase mutant.

Beneficial effects of the disclosure are further described below in combination with the embodiments.

Embodiment 1

16 mg of (1-(3-chlorophenyl)cyclopropyl)methyl sulfide is added to 10 mL of a reaction flask, 0.1 M of Tris-HCl 9.0, 20 mg of isopropanol, 0.16 mg of NADP+, 1.6 mg of alcohol dehydrogenase freeze-dried enzyme powder, and 1.6 mg of monooxygenase BVMO freeze-dried enzyme powder are added, and mixed uniformly. A total volume is 1 mL. It is reacted at 30° C. on a 200-revolution shaker for 16 hours. 3 mL of acetonitrile is added to a reaction sample system, it is placed in 5 mL of an EP tube after mixing uniformly, and centrifuged at 12,000 rpm for 3 minutes. 100 μL of supernatant is taken and put in a sample delivery bottle, 900 μL of 90% acetonitrile is added, and it is detected by HPLC with a detection wavelength of 210 nm. Results are shown in Table 1.

TABLE 1

| Mutant | Activity | Sulfone content |
|---|---|---|
| WT | − | * |
| M45T | + | * |
| V95I | + | ** |
| C106S | + | * |
| T108S | + | * |
| M114L | + | * |
| M186I | + | * |
| P190F | + | ** |
| P190L | ++ | ** |
| L191V | + | ** |
| C249V | + | * |
| C257A | + | * |
| C393V | + | * |
| C436S | + | * |
| L499A | + | ** |
| G500L | ++ | ** |
| S501T | + | ** |

TABLE 1-continued

| Mutant | Activity | Sulfone content |
|---|---|---|
| I503A | + | ** |
| Y559F | +++ | ** |
| Y559L | ++ | *** |
| Y559A | +++ | *** |
| Y560F | +++ | *** |
| Y560L | ++ | *** |
| Y560A | ++ | ** |

Compared with the SEQ ID NO: 1, the enzyme activity is improved by multiple times, + represents 1-2 times of improvement, ++ represents 3-5 times of improvement, and +++ represents 5-10 times of improvement.
20-30% of the sulfone content is represented by *, 2-20% of the content is represented by , and less than 2% of the content is represented by *.

Enzyme solution preparation method: a supernatant medium is removed by centrifugation in a 96-well plate, 200 μL of enzymatic hydrolysis solution (lysozyme 2 mg/mL, polymyxin 0.5 mg/mL, pH=7.0) is added to each well, a temperature is kept at 37° C. for 3 h.

High-throughput screening method: 250 μL bioassay system: 2 mM of a substrate final concentration, 0.3 mM of a NADPH final concentration, 100 μL of an addition amount of cell lysate enzyme solution, pH=9.0, and 30° C. of a temperature.

The mutant obtained by screening is cultured in a shake flask, and then subjected to an amplification reaction.

The best conditions for inducing the expression of the monooxygenase: 25° C., inducing with 0.1 mM IPTG overnight.

Embodiment 2

20 mg of (1-(3-chlorophenyl)cyclopropyl)methyl sulfide is added to 10 mL of a reaction flask, 0.1 M of Tris-HCl 9.0, 20 mg of isopropanol, 0.2 mg of NADP+, 20 mg of an alcohol dehydrogenase, and 20 mg of a monooxygenase BVMO are added, and mixed uniformly. A total volume is 1 mL. It is reacted at 30° C. on a 200-revolution shaker for 16 hours. 3 mL of acetonitrile is added to a reaction sample system, it is placed in 5 mL of an EP tube after mixing uniformly, and centrifuged at 12,000 rpm for 3 minutes. 100 μL of supernatant is taken and put in a sample delivery bottle, 900 μL of 90% acetonitrile is added, and it is detected by HPLC with a detection wavelength of 210 nm.

A transformation effect of a single-site mutant is higher than that of a female parent, but it does not achieve the desired effect. A combined saturation mutation may obtain a mutant with a synergistic effect between several mutation sites, and compositions of an amino acid thereof may be optimized and combined. Results are shown in Table 2.

TABLE 2

| Mutant | Activity | Sulfone content |
|---|---|---|
| WT | – | * |
| P190Q + Y560F | ++ | ** |
| P190G + Y560F | +++ | ** |
| P190R + Y560F | + | * |
| P190N + Y560F | +++ | * |
| P190F + Y560F | + | *** |
| P190E + Y560F | +++ | * |
| P190V + Y560F | +++ | *** |
| P190T + Y560F | +++ | ** |
| P190L + Y560F | ++++ | ** |
| P190I + Y560F | ++++ | *** |
| P190H + Y560F | ++++ | *** |
| P190Y + Y560F | ++++ | ** |
| Y559K + P190L | ++++ | *** |
| Y559M + P190L | +++++ | *** |
| Y559P + P190L | ++++ | ** |
| Y559Q + P190L | ++++ | *** |
| Y559L + P190L | ++++ | ** |
| Y559N + P190L | ++++ | ** |
| Y559T + P190L | ++++ | ** |
| Y559R + P190L | ++++ | ** |
| Y559V + P190L | ++++ | ** |
| Y559D + P190L | +++ | ** |
| Y559I + P190L | ++++ | ** |
| Y559A + P190L | ++++ | *** |
| Y559S + P190L | ++++ | ** |
| Y560L + P190L | +++++ | *** |
| Y560S + P190L | +++ | ** |
| Y560P + P190L | +++ | ** |
| Y559A + Y560M + P190L | ++++ | ** |
| Y559A + Y560F + P190L | ++++ | *** |
| Y559A + Y560L + P190L | ++++ | *** |
| Y559F + Y560F + P190L | +++ | ** |
| Y559F + Y560L + P190L | +++ | ** |
| Y559H + Y560L + P190L | ++++ | *** |
| Y559K + Y560L + P190L | ++++ | *** |
| Y559L + Y560F + P190L | +++ | ** |
| Y559L + Y560L + P190L | +++ | *** |
| Y559Q + Y560F + P190L | ++++ | *** |
| Y559M + Y560F + P190L | +++++ | ** |
| Y559N + Y560L + P190L | ++++ | *** |
| Y559P + Y560L + P190L | +++ | ** |
| Y559Q + Y560L + P190L | ++++ | *** |
| Y559S + Y560F + P190L | +++ | ** |
| Y559S + Y560L + P190L | ++++ | *** |
| Y559S + Y560P + P190L | + | ** |
| Y559T + Y560F + P190L | +++ | ** |
| Y559T + Y560G + P190L | + | ** |
| Y559T + Y560L + P190L | +++ | ** |
| Y559V + Y560A + P190L | ++ | * |
| Y559V + Y560F + P190L | +++ | * |
| Y559V + Y560L + P190L | ++++ | *** |
| Y559V + Y560Q + P190L | ++ | ** |
| Y559M + P190L + P504A | +++ | *** |
| Y559M + P190L + P504I | ++ | *** |
| Y559M + P190L + N503V | +++ | *** |
| Y559M + P190L + P504T | +++++ | *** |
| Y559M + P190L + P504V | ++++ | ** |
| Y559M + P190L + P504S | ++++ | ** |

Compared with the SEQ ID NO: 1, the enzyme activity is improved by multiple times, + represents 1-2 times of improvement, ++ represents 3-5 times of improvement, +++ represents 5-10 times of improvement, ++++ represents 10-20 times of improvement, and +++++ represents 20 times of improvement.
20-30% of the sulfone content is represented by *, 2-20% of the content is represented by , and less than 2% of the content is represented by *.

Combination of mutation sites may obtain the better mutant. Therefore, the mutation sites are randomly recombined by a method of DNA shuffling, to build a mutation library, and then it is screened to try to get the better mutant.

DNA shuffling is sexual recombination of genes at a molecular level. A group of homologous genes are digested with a nuclease I into random fragments, a library is formed by these random fragments, and PCR amplification is performed by using these random fragments as primers and templates mutually. While one gene copy fragment is used as a primer for another gene copy, template exchange and gene recombination occur.

Enzyme solution preparation method: a supernatant medium is removed by centrifugation in a 96-well plate, 200 μL of enzymatic hydrolysis solution (lysozyme 2 mg/mL, polymyxin 0.5 mg/mL, pH=7.0) is added to each well, a temperature is kept at 37° C. for 3 h.

High-throughput screening method: 250 μL bioassay system: 2 mM of a substrate final concentration, 0.3 mM of a NADPH final concentration, 100 μL of an addition amount of cell lysate enzyme solution, pH=9.0, and 30° C. of a temperature.

The mutant obtained by screening is cultured in a shake flask, and then subjected to an amplification reaction.

The best conditions for inducing the expression of the monooxygenase: 25° C., inducing with 0.1 mM IPTG overnight.

Embodiment 3

30 mg of (1-(3-chlorophenyl)cyclopropyl)methyl sulfide is added to 10 mL of a reaction flask, 0.1 M of Tris-HCl 9.0, 30 mg of isopropanol, 0.3 mg of NADP+, 30 mg of an alcohol dehydrogenase, and 30 mg of a monooxygenase BVMO are added, and mixed uniformly. A total volume is 1 mL. It is reacted at 30° C. on a 200-revolution shaker for 16 hours. 3 mL of acetonitrile is added to a reaction sample system, it is placed in 5 mL of an EP tube after mixing uniformly, and centrifuged at 12,000 rpm for 3 minutes. 100 μL of supernatant is taken and put in a sample delivery bottle, 900 μL of 90% acetonitrile is added, and it is detected by HPLC with a detection wavelength of 210 nm. Results are shown in Table 3.

TABLE 3

| Mutant | Activity | Sulfone content |
|---|---|---|
| WT | – | * |
| P190L + Y559M + M45T | +++++ | *** |
| P190L + Y559M + C257A | +++++ | *** |
| P190L + Y559M + C249V | +++++ | *** |
| P190L + Y559M + C393V | +++++ | *** |
| P190L + Y559M + M186I | +++++ | *** |
| P190L + Y559M + C249V + C393V | +++++ | *** |
| P190L + Y559M + C249V + C393V + C257A | +++++ | *** |
| P190L + Y559M + C249V + C393V + C257A + M45T | +++++ | *** |
| P190L + Y559M + C249V + C393V + C257A + M45T + M186I | +++++ | *** |

Compared with the SEQ ID NO: 1, the enzyme activity is improved by multiple times, + represents 1-2 times of improvement, ++ represents 3-5 times of improvement, +++ represents 5-10 times of improvement, ++++ represents 10-20 times of improvement, and +++++ represents 20 times of improvement.
20-30% of the sulfone content is represented by *, 2-20% of the content is represented by , and less than 2% of the content is represented by *.

The above are only preferred embodiments of the disclosure, and are not intended to limit the disclosure. Various modifications and changes may be made to the disclosure by those skilled in the art. Any modifications, equivalent replacements, improvements and the like made within the spirit and principle of the disclosure should be included in a scope of protection of the disclosure.

The invention claimed is:

1. A monooxygenase mutant having monooxygenase activity, wherein the monooxygenase mutant comprises all of SEQ ID NO: 1 except for one of the substitutions selected from the group consisting of:

the amino acid at the position corresponding to position 559 of the polypeptide of SEQ ID NO: 1 is replaced with lysine and the amino acid at the position corresponding to position 190 of the polypeptide of SEQ ID NO: 1 is replaced with leucine;

the amino acid at the position corresponding to position 559 of the polypeptide of SEQ ID NO: 1 is replaced with methionine and the amino acid at the position corresponding to position 190 of the polypeptide of SEQ ID NO: 1 is replaced with leucine;

the amino acid at the position corresponding to position 559 of the polypeptide of SEQ ID NO: 1 is replaced with proline and the amino acid at the position corresponding to position 190 of the polypeptide of SEQ ID NO: 1 is replaced with leucine;

the amino acid at the position corresponding to position 559 of the polypeptide of SEQ ID NO: 1 is replaced with glutamine and the amino acid at the position corresponding to position 190 of the polypeptide of SEQ ID NO: 1 is replaced with leucine;

the amino acid at the position corresponding to position 559 of the polypeptide of SEQ ID NO: 1 is replaced with leucine and the amino acid at the position corresponding to position 190 of the polypeptide of SEQ ID NO: 1 is replaced with leucine;

the amino acid at the position corresponding to position 559 of the polypeptide of SEQ ID NO: 1 is replaced with asparagine and the amino acid at the position corresponding to position 190 of the polypeptide of SEQ ID NO: 1 is replaced with leucine;

the amino acid at the position corresponding to position 559 of the polypeptide of SEQ ID NO: 1 is replaced with threonine and the amino acid at the position corresponding to position 190 of the polypeptide of SEQ ID NO: 1 is replaced with leucine;

the amino acid at the position corresponding to position 559 of the polypeptide of SEQ ID NO: 1 is replaced with arginine and the amino acid at the position corresponding to position 190 of the polypeptide of SEQ ID NO: 1 is replaced with leucine;

the amino acid at the position corresponding to position 559 of the polypeptide of SEQ ID NO: 1 is replaced with valine and the amino acid at the position corresponding to position 190 of the polypeptide of SEQ ID NO: 1 is replaced with leucine;

the amino acid at the position corresponding to position 559 of the polypeptide of SEQ ID NO: 1 is replaced with aspartic acid and the amino acid at the position corresponding to position 190 of the polypeptide of SEQ ID NO: 1 is replaced with leucine;

the amino acid at the position corresponding to position 559 of the polypeptide of SEQ ID NO: 1 is replaced with isoleucine and the amino acid at the position corresponding to position 190 of the polypeptide of SEQ ID NO: 1 is replaced with leucine;

the amino acid at the position corresponding to position 559 of the polypeptide of SEQ ID NO: 1 is replaced with alanine and the amino acid at the position corresponding to position 190 of the polypeptide of SEQ ID NO: 1 is replaced with leucine;

the amino acid at the position corresponding to position 559 of the polypeptide of SEQ ID NO: 1 is replaced with serine and the amino acid at the position corresponding to position 190 of the polypeptide of SEQ ID NO: 1 is replaced with leucine;

the amino acid at the position corresponding to position 559 of the polypeptide of SEQ ID NO: 1 is replaced with alanine, the amino acid at the position corresponding to position 560 of the polypeptide of SEQ ID NO: 1 is replaced with methionine and the amino acid at the position corresponding to position 190 of the polypeptide of SEQ ID NO: 1 is replaced with leucine;

the amino acid at the position corresponding to position 559 of the polypeptide of SEQ ID NO: 1 is replaced with alanine, the amino acid at the position corresponding to position 560 of the polypeptide of SEQ ID NO: 1 is replaced with phenylalanine and the amino acid at the position corresponding to position 190 of the polypeptide of SEQ ID NO: 1 is replaced with leucine;

the amino acid at the position corresponding to position 559 of the polypeptide of SEQ ID NO: 1 is replaced with alanine, the amino acid at the position corresponding to position 560 of the polypeptide of SEQ ID NO: 1 is replaced with leucine and the amino acid at the position corresponding to position 190 of the polypeptide of SEQ ID NO: 1 is replaced with leucine;

the amino acid at the position corresponding to position 559 of the polypeptide of SEQ ID NO: 1 is replaced with phenylalanine, the amino acid at the position corresponding to position 560 of the polypeptide of SEQ ID NO: 1 is replaced with phenylalanine and the amino acid at the position corresponding to position 190 of the polypeptide of SEQ ID NO: 1 is replaced with leucine;

the amino acid at the position corresponding to position 559 of the polypeptide of SEQ ID NO: 1 is replaced with phenylalanine, the amino acid at the position corresponding to position 560 of the polypeptide of SEQ ID NO: 1 is replaced with leucine and the amino acid at the position corresponding to position 190 of the polypeptide of SEQ ID NO: 1 is replaced with leucine;

the amino acid at the position corresponding to position 559 of the polypeptide of SEQ ID NO: 1 is replaced with histidine, the amino acid at the position corresponding to position 560 of the polypeptide of SEQ ID NO: 1 is replaced with leucine and the amino acid at the position corresponding to position 190 of the polypeptide of SEQ ID NO: 1 is replaced with leucine;

the amino acid at the position corresponding to position 559 of the polypeptide of SEQ ID NO: 1 is replaced with lysine, the amino acid at the position corresponding to position 560 of the polypeptide of SEQ ID NO: 1 is replaced with leucine and the amino acid at the position corresponding to position 190 of the polypeptide of SEQ ID NO: 1 is replaced with leucine;

the amino acid at the position corresponding to position 559 of the polypeptide of SEQ ID NO: 1 is replaced with leucine, the amino acid at the position corresponding to position 560 of the polypeptide of SEQ ID NO: 1 is replaced with phenylalanine and the amino acid at the position corresponding to position 190 of the polypeptide of SEQ ID NO: 1 is replaced with leucine;

the amino acid at the position corresponding to position 559 of the polypeptide of SEQ ID NO: 1 is replaced with leucine, the amino acid at the position corresponding to position 560 of the polypeptide of SEQ ID NO: 1 is replaced with leucine and the amino acid at the position corresponding to position 190 of the polypeptide of SEQ ID NO: 1 is replaced with leucine;

the amino acid at the position corresponding to position 559 of the polypeptide of SEQ ID NO: 1 is replaced with glutamine, the amino acid at the position corresponding to position 560 of the polypeptide of SEQ ID NO: 1 is replaced with phenylalanine and the amino acid at the position corresponding to position 190 of the polypeptide of SEQ ID NO: 1 is replaced with leucine;

the amino acid at the position corresponding to position 559 of the polypeptide of SEQ ID NO: 1 is replaced with methionine, the amino acid at the position corresponding to position 560 of the polypeptide of SEQ ID NO: 1 is replaced with phenylalanine and the amino acid at the position corresponding to position 190 of the polypeptide of SEQ ID NO: 1 is replaced with leucine;

the amino acid at the position corresponding to position 559 of the polypeptide of SEQ ID NO: 1 is replaced with asparagine, the amino acid at the position corresponding to position 560 of the polypeptide of SEQ ID NO: 1 is replaced with leucine and the amino acid at the position corresponding to position 190 of the polypeptide of SEQ ID NO: 1 is replaced with leucine;

the amino acid at the position corresponding to position 559 of the polypeptide of SEQ ID NO: 1 is replaced with proline, the amino acid at the position corresponding to position 560 of the polypeptide of SEQ ID NO: 1 is replaced with leucine and the amino acid at the position corresponding to position 190 of the polypeptide of SEQ ID NO: 1 is replaced with leucine;

the amino acid at the position corresponding to position 559 of the polypeptide of SEQ ID NO: 1 is replaced with glutamine, the amino acid at the position corresponding to position 560 of the polypeptide of SEQ ID NO: 1 is replaced with leucine and the amino acid at the position corresponding to position 190 of the polypeptide of SEQ ID NO: 1 is replaced with leucine;

the amino acid at the position corresponding to position 559 of the polypeptide of SEQ ID NO: 1 is replaced with serine, the amino acid at the position corresponding to position 560 of the polypeptide of SEQ ID NO: 1 is replaced with phenylalanine and the amino acid at the position corresponding to position 190 of the polypeptide of SEQ ID NO: 1 is replaced with leucine;

the amino acid at the position corresponding to position 559 of the polypeptide of SEQ ID NO: 1 is replaced with serine, the amino acid at the position corresponding to position 560 of the polypeptide of SEQ ID NO: 1 is replaced with leucine and the amino acid at the position corresponding to position 190 of the polypeptide of SEQ ID NO: 1 is replaced with leucine;

the amino acid at the position corresponding to position 559 of the polypeptide of SEQ ID NO: 1 is replaced with serine, the amino acid at the position corresponding to position 560 of the polypeptide of SEQ ID NO: 1 is replaced with proline and the amino acid at the position corresponding to position 190 of the polypeptide of SEQ ID NO: 1 is replaced with leucine;

the amino acid at the position corresponding to position 559 of the polypeptide of SEQ ID NO: 1 is replaced with threonine, the amino acid at the position corresponding to position 560 of the polypeptide of SEQ ID NO: 1 is replaced with phenylalanine and the amino acid at the position corresponding to position 190 of the polypeptide of SEQ ID NO: 1 is replaced with leucine;

the amino acid at the position corresponding to position 559 of the polypeptide of SEQ ID NO: 1 is replaced with threonine, the amino acid at the position corresponding to position 560 of the polypeptide of SEQ ID NO: 1 is replaced with glycine and the amino acid at the position corresponding to position 190 of the polypeptide of SEQ ID NO: 1 is replaced with leucine;

the amino acid at the position corresponding to position 559 of the polypeptide of SEQ ID NO: 1 is replaced with threonine, the amino acid at the position corresponding to position 560 of the polypeptide of SEQ ID NO: 1 is replaced with leucine and the amino acid at the position corresponding to position 190 of the polypeptide of SEQ ID NO: 1 is replaced with leucine;

the amino acid at the position corresponding to position 559 of the polypeptide of SEQ ID NO: 1 is replaced with valine, the amino acid at the position corresponding to position 560 of the polypeptide of SEQ ID NO: 1 is replaced with alanine and the amino acid at the position corresponding to position 190 of the polypeptide of SEQ ID NO: 1 is replaced with leucine;

the amino acid at the position corresponding to position 559 of the polypeptide of SEQ ID NO: 1 is replaced with valine, the amino acid at the position corresponding to position 560 of the polypeptide of SEQ ID NO: 1 is replaced with phenylalanine and the amino acid at the position corresponding to position 190 of the polypeptide of SEQ ID NO: 1 is replaced with leucine;

the amino acid at the position corresponding to position 559 of the polypeptide of SEQ ID NO: 1 is replaced with valine, the amino acid at the position corresponding to position 560 of the polypeptide of SEQ ID NO: 1 is replaced with leucine and the amino acid at the position corresponding to position 190 of the polypeptide of SEQ ID NO: 1 is replaced with leucine;

the amino acid at the position corresponding to position 559 of the polypeptide of SEQ ID NO: 1 is replaced with valine, the amino acid at the position corresponding to position 560 of the polypeptide of SEQ ID NO: 1 is replaced with glutamine and the amino acid at the position corresponding to position 190 of the polypeptide of SEQ ID NO: 1 is replaced with leucine;

the amino acid at the position corresponding to position 559 of the polypeptide of SEQ ID NO: 1 is replaced with methionine, the amino acid at the position corresponding to position 504 of the polypeptide of SEQ ID NO: 1 is replaced with alanine and the amino acid at the position corresponding to position 190 of the polypeptide of SEQ ID NO: 1 is replaced with leucine;

the amino acid at the position corresponding to position 559 of the polypeptide of SEQ ID NO: 1 is replaced with methionine, the amino acid at the position corresponding to position 504 of the polypeptide of SEQ ID NO: 1 is replaced with isoleucine and the amino acid at the position corresponding to position 190 of the polypeptide of SEQ ID NO: 1 is replaced with leucine;

the amino acid at the position corresponding to position 559 of the polypeptide of SEQ ID NO: 1 is replaced with methionine, the amino acid at the position corresponding to position 503 of the polypeptide of SEQ ID NO: 1 is replaced with valine and the amino acid at the position corresponding to position 190 of the polypeptide of SEQ ID NO: 1 is replaced with leucine;

the amino acid at the position corresponding to position 559 of the polypeptide of SEQ ID NO: 1 is replaced with methionine, the amino acid at the position corresponding to position 504 of the polypeptide of SEQ ID NO: 1 is replaced with threonine and the amino acid at the position corresponding to position 190 of the polypeptide of SEQ ID NO: 1 is replaced with leucine;

the amino acid at the position corresponding to position 559 of the polypeptide of SEQ ID NO: 1 is replaced with methionine, the amino acid at the position corresponding to position 504 of the polypeptide of SEQ ID NO: 1 is replaced with valine and the amino acid at the position corresponding to position 190 of the polypeptide of SEQ ID NO: 1 is replaced with leucine;

the amino acid at the position corresponding to position 559 of the polypeptide of SEQ ID NO: 1 is replaced with methionine, the amino acid at the position corresponding to position 504 of the polypeptide of SEQ ID NO: 1 is replaced with serine and the amino acid at the position corresponding to position 190 of the polypeptide of SEQ ID NO: 1 is replaced with leucine;

the amino acid at the position corresponding to position 190 of the polypeptide of SEQ ID NO: 1 is replaced with leucine, the amino acid at the position corresponding to position 559 of the polypeptide of SEQ ID NO:

1 is replaced with methionine and the amino acid at the position corresponding to position 45 of the polypeptide of SEQ ID NO: 1 is replaced with threonine;

the amino acid at the position corresponding to position 190 of the polypeptide of SEQ ID NO: 1 is replaced with leucine, the amino acid at the position corresponding to position 559 of the polypeptide of SEQ ID NO: 1 is replaced with methionine and the amino acid at the position corresponding to position 257 of the polypeptide of SEQ ID NO: 1 is replaced with alanine;

the amino acid at the position corresponding to position 190 of the polypeptide of SEQ ID NO: 1 is replaced with leucine, the amino acid at the position corresponding to position 559 of the polypeptide of SEQ ID NO: 1 is replaced with methionine and the amino acid at the position corresponding to position 249 of the polypeptide of SEQ ID NO: 1 is replaced with valine;

the amino acid at the position corresponding to position 190 of the polypeptide of SEQ ID NO: 1 is replaced with leucine, the amino acid at the position corresponding to position 559 of the polypeptide of SEQ ID NO: 1 is replaced with methionine and the amino acid at the position corresponding to position 393 of the polypeptide of SEQ ID NO: 1 is replaced with valine;

the amino acid at the position corresponding to position 190 of the polypeptide of SEQ ID NO: 1 is replaced with leucine, the amino acid at the position corresponding to position 559 of the polypeptide of SEQ ID NO: 1 is replaced with methionine and the amino acid at the position corresponding to position 186 of the polypeptide of SEQ ID NO: 1 is replaced with isoleucine;

the amino acid at the position corresponding to position 190 of the polypeptide of SEQ ID NO: 1 is replaced with leucine, the amino acid at the position corresponding to position 559 of the polypeptide of SEQ ID NO: 1 is replaced with methionine, the amino acid at the position corresponding to position 249 of the polypeptide of SEQ ID NO: 1 is replaced with valine and the amino acid at the position corresponding to position 393 of the polypeptide of SEQ ID NO: 1 is replaced with valine;

the amino acid at the position corresponding to position 190 of the polypeptide of SEQ ID NO: 1 is replaced with leucine, the amino acid at the position corresponding to position 559 of the polypeptide of SEQ ID NO: 1 is replaced with methionine, the amino acid at the position corresponding to position 249 of the polypeptide of SEQ ID NO: 1 is replaced with valine, the amino acid at the position corresponding to position 393 of the polypeptide of SEQ ID NO: 1 is replaced with valine and the amino acid at the position corresponding to position 257 of the polypeptide of SEQ ID NO: 1 is replaced with alanine;

the amino acid at the position corresponding to position 190 of the polypeptide of SEQ ID NO: 1 is replaced with leucine, the amino acid at the position corresponding to position 559 of the polypeptide of SEQ ID NO: 1 is replaced with methionine, the amino acid at the position corresponding to position 249 of the polypeptide of SEQ ID NO: 1 is replaced with valine, the amino acid at the position corresponding to position 393 of the polypeptide of SEQ ID NO: 1 is replaced with valine, the amino acid at the position corresponding to position 257 of the polypeptide of SEQ ID NO: 1 is replaced with alanine and the amino acid at the position corresponding to position 45 of the polypeptide of SEQ ID NO: 1 is replaced with threonine; and the amino acid at the position corresponding to position 190 of the polypeptide of SEQ ID NO: 1 is replaced with leucine, the amino acid at the position corresponding to position 559 of the polypeptide of SEQ ID NO: 1 is replaced with methionine, the amino acid at the position corresponding to position 249 of the polypeptide of SEQ ID NO: 1 is replaced with valine, the amino acid at the position corresponding to position 393 of the polypeptide of SEQ ID NO: 1 is replaced with valine, the amino acid at the position corresponding to position 257 of the polypeptide of SEQ ID NO: 1 is replaced with alanine, the amino acid at the position corresponding to position 45 of the polypeptide of SEQ ID NO: 1 is replaced with threonine and the amino acid at the position corresponding to position 186 of the polypeptide of SEQ ID NO: 1 is replaced with isoleucine.

2. A method for producing a chiral sulfoxide, comprising a step of performing a catalytic monooxygenation reaction on a thioether compound by a monooxygenase, wherein the monooxygenase is the monooxygenase mutant according to claim 1, and the thioether compound is

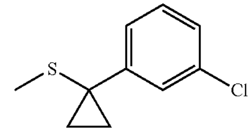

((1-(3-chlorophenyl)cyclopropyl)methyl sulfide).

3. The method according to claim 2, wherein the monooxygenase is in the form of an enzyme solution, a whole cell, freeze-dried enzyme powder, a freeze-dried cell, an immobilized enzyme or an immobilized cell.

4. The method according to claim 2, wherein the catalytic monooxygenation reaction requires a cofactor circulation system, wherein the cofactor circulation system is a NAD/NADH or a NADP/NADPH cofactor circulation system, and wherein the cofactor circulation system comprises (i) glucose and glucose dehydrogenase, (ii) formate and formate dehydrogenase, (iii) glucose-6-phosphate and glucose-6-phosphate dehydrogenase, or (iv) a secondary alcohol and a secondary alcohol dehydrogenase.

5. The method according to claim 2, wherein the amount of the monooxygenase in the catalytic monooxygenation reaction is 0.1 to 10 times the amount of the thioether.

6. The method according to claim 2, wherein the temperature of the monooxygenation reaction is 10-50° C.

7. The method according to claim 2, wherein the monooxygenation reaction is performed at a pH of 7-10.

8. The method according to claim 2, wherein the temperature of the monooxygenation reaction is 30° C.

9. The method according to claim 2, wherein the monooxygenation reaction is performed at a pH of 9.

* * * * *